US008605293B2

(12) United States Patent
Knobbe

(10) Patent No.: US 8,605,293 B2
(45) Date of Patent: Dec. 10, 2013

(54) POSITION SENSOR

(75) Inventor: Jens Knobbe, Dresden (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 189 days.

(21) Appl. No.: 13/154,630

(22) Filed: Jun. 7, 2011

(65) Prior Publication Data

US 2011/0299096 A1 Dec. 8, 2011

(30) Foreign Application Priority Data

Jun. 8, 2010 (DE) .......................... 10 2010 029 818

(51) Int. Cl.
*G01B 11/14* (2006.01)
(52) U.S. Cl.
USPC .......................................... 356/614; 356/620
(58) Field of Classification Search
USPC ........ 356/614–615, 619–623, 73.1, 138, 912; 600/117; 250/205, 201.1; 73/655, 649
See application file for complete search history.

(56) References Cited

U.S. PATENT DOCUMENTS

| 3,432,671 | A |   | 3/1969  | Edmonds |
| 4,358,960 | A | * | 11/1982 | Porter .............................. 73/705 |
| 4,581,528 | A |   | 4/1986  | Brogardh et al. |
| 6,118,521 | A | * | 9/2000  | Jung et al. ........................ 356/73 |
| 7,619,752 | B2 | * | 11/2009 | Liphardt et al. ............... 356/620 |
| 2007/0081168 | A1 |   | 4/2007  | Johnston |

FOREIGN PATENT DOCUMENTS

| DE | 102 05 207 A1 | 8/2003 |
| DE | 103 57 062 A1 | 7/2005 |

* cited by examiner

*Primary Examiner* — Tri T Ton
(74) *Attorney, Agent, or Firm* — Keating & Bennett, LLP

(57) ABSTRACT

A position sensor for detecting a position of a movably arranged component with respect to its original position including a channel which is implemented to guide electromagnetic radiation and direct the same to the component, a detector, at least two back channels which are implemented to receive the electromagnetic radiation reflected by the device and direct the same to the detector, wherein the channel and the at least two back channels are arranged with respect to each other such that the at least two back channels each receive a predefined portion of the electromagnetic radiation reflected by the component.

14 Claims, 9 Drawing Sheets

POSITION SENSOR

CROSS-REFERENCE TO RELATED APPLICATIONS

This application claims priority from German Patent Application No. 102010029818.2-52, which was filed on Jun. 8, 2010, and is incorporated herein in its entirety by reference.

BACKGROUND OF THE INVENTION

Embodiments of the invention relate to the field of position determination, in particular a position sensor for the determination of the state of deflection of a movably arranged mechanical component.

According to conventional technology, different categories of position sensors for determining the deflection state of a mechanical component are known. Discretely assembled optical or electric/magnetic sensors, but also integrated sensors are known.

Incremental encoders are part of the category of discretely assembled optical or electric/magnetic position sensors. The same are used both for translationally and also for rotationally movably arranged mechanical components. The functioning of incremental encoders is based on an exact scanning of optical or magnetic scales. Depending on the assembly and implementation, position sensors based on incremental encoders are able to determine the position or the deflection state of a mechanical component very accurately, however they need a comparatively large design space. For this reason, incremental encoders are mainly used in macroscopic devices, like, e.g., in turntables and positioning tables. For use in miniaturized systems, in particular for use in endoscopic applications, position sensors based on incremental encoders are not suitable, however.

For small mechanical components, like, e.g., for microscanner mirrors, further discretely assembled optical devices are known, so-called free beam arrangements. In a free beam arrangement, the measurement of the deflection state of a movably arranged mechanical component is generally executed with the help of a laser beam. The laser beam is directed at the mechanical component and reflected or deflected by the mechanical component, depending on the current deflection of the component, in different directions. For determining the position of the deflection state of the mechanical component, the laser beam reflected by the component is detected by photodetectors positioned in a suitable way. A disadvantage of the free beam arrangements is the needed large building space. Laser diodes and photodiodes as well as further optical components needed for beam shaping have to be arranged directly around the mechanical component. Further, in free beam arrangements trigger diodes are partially used as detectors. Trigger diodes only enable the execution of time-discrete measurements, using which no statistical deflections of the mechanical component can be determined. For the above-mentioned reasons, position sensors based on free beam arrangements are not suitable for being used in miniaturized systems, in particular for use in endoscopic applications.

A further category of position sensors includes integrated sensors for determining the deflection state of a movably arranged mechanical component. Capacitive position sensors contain capacitive structures suitably integrated into the component or connected to the component. A change of the deflection state of the mechanical component causes a measurable change in the electric capacity. Capacitive position sensors are, however, relatively inaccurate. Further, in microsystem mechanics many components, like, e.g., microscanner mirrors, are driven electrostatically, so that it is difficult to separate the relatively high drive voltages sufficiently from the measurement signals. A sufficiently accurate determination of the position or the deflection state of a movably arranged mechanical component is not possible with capacitive position sensors.

Further, in microsystem technology, piezoresistive methods are known for determining the deflection state of a movably arranged mechanical component. For this method, however, there is also the problem of sufficiently separating the relatively high drive voltages from the measurement signals. The overlaying of the drive voltage with the measurement signals may be disadvantageous for the measurement resolution and thus for the determination of the position or the deflection state of the mechanical component.

Further, integrated capacitive and piezoresistive sensors need electronic circuits in the direct vicinity of the mechanical component for amplifying the measurement signals, as the unamplified measurement signals may not be transmitted over distances of any length. For this reason, position sensors based on integrated capacitive and piezoresistive sensors are not suitable for use in endoscopes which need small lateral dimensions and relatively long transmission distances of the measurement signals.

SUMMARY

According to an embodiment, a position sensor for detecting a position of a movably arranged component with respect to its original position may have at least one channel which is implemented to guide electromagnetic radiation and direct the same to the component; at least one detector; and at least two back channels which are implemented to receive electromagnetic radiation reflected by the component and direct the same to the detector, wherein the channel and the at least two back channels are arranged with respect to each other such that the at least two back channels each receive a predefined portion of the electromagnetic radiation reflected by the component.

According to another embodiment, a device may have a component which is supported rotatably around at least one axis, and a position sensor for detecting a position of a movably arranged component with respect to its original position which may have at least one channel which is implemented to guide electromagnetic radiation and direct the same to the component; at least one detector; and at least two back channels which are implemented to receive electromagnetic radiation reflected by the component and direct the same to the detector, wherein the channel and the at least two back channels are arranged with respect to each other such that the at least two back channels each receive a predefined portion of the electromagnetic radiation reflected by the component.

The invention provides a position sensor for detecting the position of a movably arranged component with respect to its original position, comprising a channel implemented to guide electromagnetic radiation and direct the same at the component;

a detector; and at least two back channels implemented to receive the electromagnetic radiation reflected by the component and direct the same to the detector, wherein the channel and the at least two back channels are arranged with respect to each other such that the at least two back channels each receive a predefined portion of the electromagnetic radiation reflected by the component.

For detecting the deflection state of the movably arranged mechanical component, the inventive position sensor uses the electromagnetic radiation of a radiation source which is coupled into the channel which is implemented to guide electromagnetic radiation and direct the same to the component. The electromagnetic radiation leaving the channel hits the mechanical component and is reflected depending on the deflection state. The back channels, depending on the deflection state of the mechanical component, receive a portion of the reflected electromagnetic radiation which leads to differently high electric signals in the respective detectors. By amplifying and evaluating the electric signals of the detectors of the back channels, the deflection state of the mechanical component may be determined.

The inventive position sensor, with respect to the conventional technology, provides the advantage of a very small building size, in particular regarding its diameter, which is why the inventive position sensor is very suitable for endoscopic applications. Further, the inventive position sensor provides the advantage of being galvanically decoupled from the drive voltages of the mechanical component. An overlaying of the measurement signals of the position sensor with the drive voltages of the mechanical component is thus prevented. Further, in the direct vicinity of the mechanical component no electronic circuits are to be provided for amplifying the measurement signals. For being used in endoscopic applications, the needed electronic circuits may, for example, be dislocated to the outside, where the needed building space plays only a subordinate role. Further, the inventive position sensor is able to determine continuous movement processes, like, e.g., movement processes caused by resonant drives, and also quasi static and static movements or deflections of the mechanical component. The temporal resolution of the position sensor is here only limited by the cutoff frequency of the used detectors and the downstream electronic circuit. These characteristics are in particular advantageous for microscanner mirrors or components based on microscanner mirrors which are used in many different variants and designs.

BRIEF DESCRIPTION OF THE DRAWINGS

In the following, embodiments of the present invention are explained in more detail with reference to the accompanying drawings, in which:

FIG. 2a show an enlarged illustration of the end portion of the optical fiber of FIGS. 1, and 2b wherein FIG. 2a shows a side view and FIG. 2b a front view of the optical fiber;

DETAILED DESCRIPTION OF THE INVENTION

Figure 1:
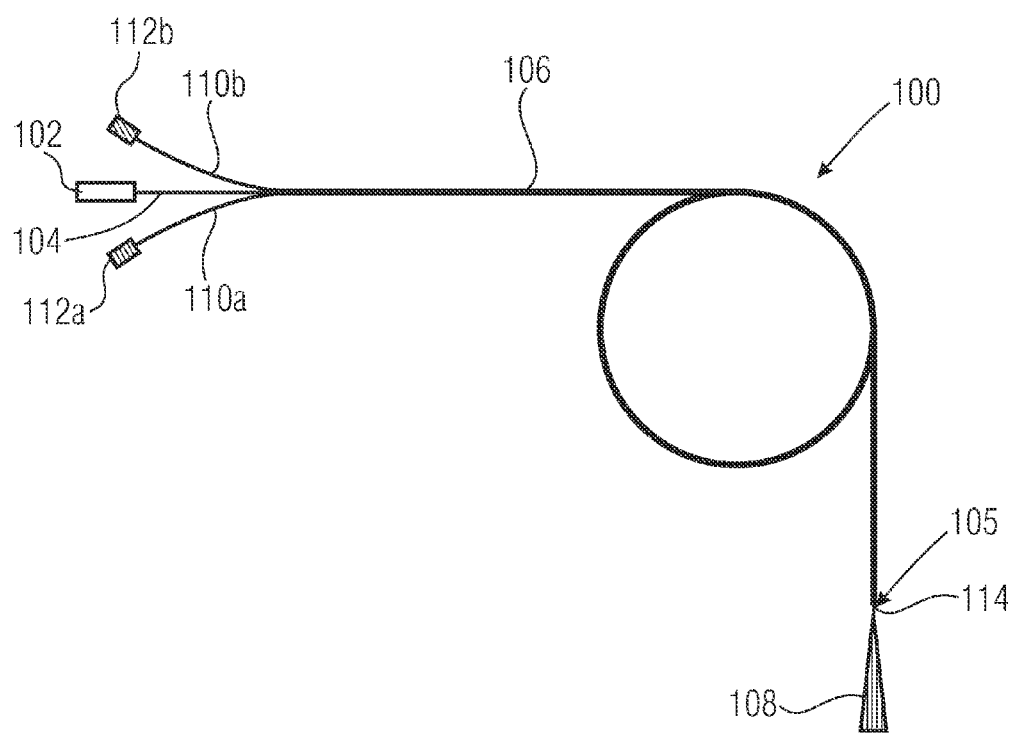
FIG. 1 shows a schematical illustration of the position sensor according to an embodiment of the invention using optical fibers for guiding the electromagnetic radiation without the mechanical component whose deflection state is to be determined.

In the following description of the embodiments of the invention, in the figures like or seemingly like elements are provided with the same reference numerals.

FIG. 1 shows a schematical illustration of the position sensor according to one embodiment of the invention using optical fibers for guiding the electromagnetic radiation without the mechanical component whose deflection state is to be determined. An electromagnetic radiation source 102 is suitably connected to an optical fiber 104 generally consisting of a glass material or a plastic material. In all illustrated embodiments, the electromagnetic radiation used for irradiating the mechanical component may be within different spectral ranges of the electromagnetic spectrum. Thus, e.g., wavelengths in the visible spectral range (VIS) are possible as well as in the infrared (IR) spectral range or in the ultraviolet (UV) spectral range. Also different radiation sources, like, e.g., LEDs or lasers may be used. For coupling the electromagnetic radiation of the radiation source 102 into the optical fiber 104, apart from that further known optical components may be needed. As an optical fiber 104, embodiments of the invention use a monomode fiber having a step-index profile. However, also multimode fibers or fibers with a different refraction index profile may be used, like, e.g., a gradient index fiber or a fiber based on photonic crystals. The electromagnetic radiation generated by the radiation source 102 is coupled into the optical fiber 104 and exits the optical fiber 104 at the end 105 of the fiber bundle 106 in the form of a beam cone 108. Two further fibers 110a and 110b are illustrated which serve for receiving electromagnetic radiation which is reflected by a mechanical component. The two optical fibers 110a and 110b, according to embodiments, are multimode fibers having a high numerical aperture and a comparatively large core diameter of up to some hundred micrometers. The optical fibers 110a and 110b may consist of different materials, like, e.g., a glass material or plastics, and are suitably connected to one detector each for electromagnetic radiation 112a and 112b, e.g. to one photodiode each. Further, the detectors for electromagnetic radiation 112a and 112b may be implemented for different spectral ranges of the electromagnetic spectrum. The detectors 112a and 112b have to be adapted to the wavelength of the radiation source 102.

The individual fibers 104, 110a and 110b may be combined into a fiber bundle 106 using conventional methods of fiber mounting. In the simplest case, the optical fibers 104, 110a and 110b are only held together by a common suitably implemented protective coating. For mounting the complete position sensor, in particular for the defined and reproducible connection of position sensor and mechanical component, conventional methods from microsystem technology and fiber technology may be used. Thus, for example, auxiliary structures for the passive adjustment of fiber bundles 106 and mechanical components are common. At the output 114 of the fiber bundle 106 (component side) small mechanical auxiliary structures may be located, e.g. a cylindrical structure, which facilitate mounting or holding of the fiber bundle 106 to the component or a common carrier or substrate and fix their position with respect to each other. Possibly, active adjustment procedures are needed in which the radiation source is taken into operation and simultaneously the electrical signals are fed out at the detectors 112a and 112b. The electrical signals are then used as adjustment criteria.

Figures 2A, 2B:
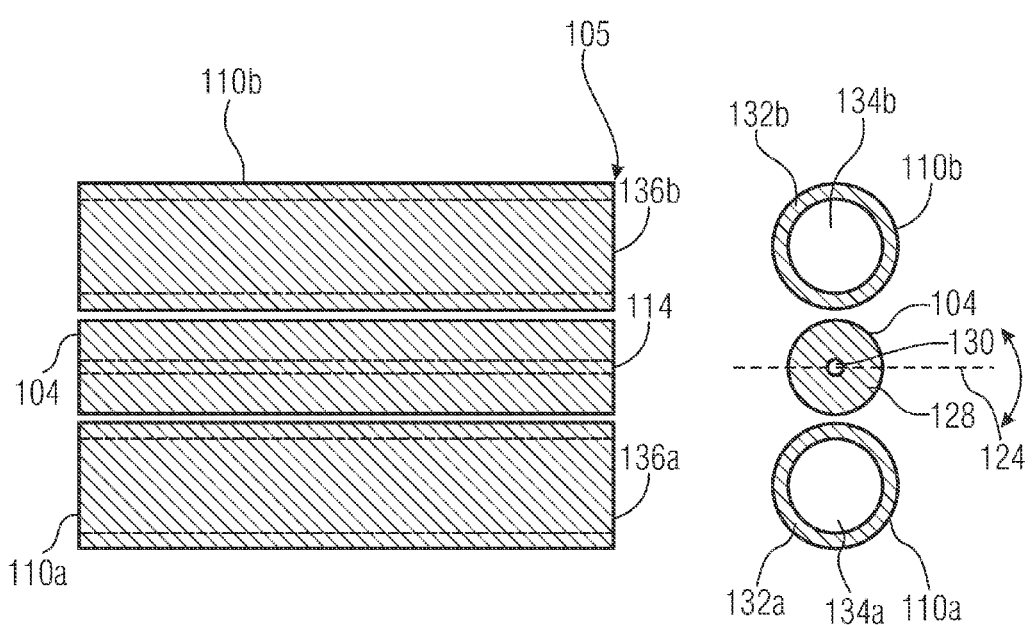

FIGS. 2a and 2b show an enlarged illustration of an end section of the optical fiber bundle 106 of FIG. 1 for the determination of the deflection state of a mechanical component around a rotational axis 124, e.g. a scanner mirror, wherein FIG. 2a shows a side view and FIG. 2b a front view of the optical fiber bundle. In the center, a monomode fiber (transmission fiber) 104 with a sheath 128 and a core 130 is arranged which outputs the electromagnetic radiation at the output 114. It may be implemented as an optical fiber having a step-index profile. Further, it may be a fiber wherein the sheath 128 and the core 130 are manufactured from a glass material (glass fiber) or wherein the sheath 128 consists of a polymer. The optical fiber 104 serves for irradiating the movably arranged mechanical component whose deflection state is to be determined. Two optical fibers (receiving fibers) 110a and 110b with the sheath 132a and 132b and the core 134a and 134b are arranged symmetrically to the transmission fiber 104 and may receive a part of the electromagnetic radiation reflected by the component at the inputs 136a and 136b. The arrangement of the optical fibers 110a and 110b is further symmetrical to the rotational axis 124 of the mechanical component. The receiving fibers 110a and 110b including the sheath 132a and 132b and the core 134a and 134b may be manufactured from a glass material. However, also the use of polymer fibers is possible, in particular ones having a core of glass and a polymer sheath. The receiving fibers 110a and 110b, according to embodiments, but not necessarily, have a high numerical aperture of greater than 0.3 and a fiber core diameter of some hundred micrometers. The symmetry of the fiber bundle 106 may here be achieved and stabilized by suitable auxiliary structures (spacers). The described embodiment comprises channels which are at least partially arranged symmetrically to each other along their extension. It is to be noted that the invention is not limited to such embodiments. In embodiments it is sufficient that the output of the channel and the inputs of the back channels are arranged in a certain relation to each other, e.g. symmetrically, to enable the defined input of the reflected radiation. The further course of the channel and the back channels is not important. In embodiments, the locations where the radiation is coupled into the channel and the radiation is coupled out of the back channels may be different.

Figure 3A:
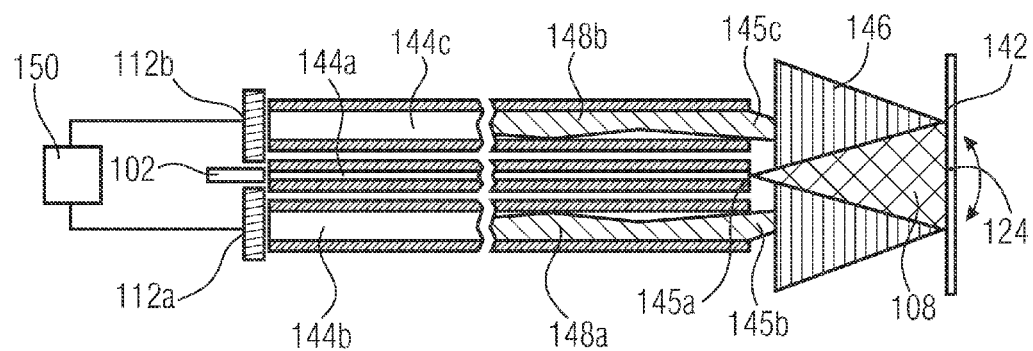
FIG. 3a show an illustration explaining the functioning of the position sensor of FIGS. 1, and 3b wherein the mechanical component is in its rest position in FIG. 3a and wherein the mechanical component is deflected from its rest position in FIG. 3b.

FIG. 3a shows an illustration which shows the functioning of the position sensor of FIG. 1 in detail, wherein the mechanical component 142 in FIG. 3a is in its rest position. In the center, a channel 144a is arranged which guides electromagnetic radiation, outputs the same at the output 145a and directs the same at the device 142. Around the channel 144a, according to embodiments, two back channels 144b and 144c are arranged in a symmetrical arrangement which may receive part of the electromagnetic radiation 146 reflected by the component at the inputs 145b and 145c. Further, an electromagnetic radiation source 102 is illustrated, e.g. an LED or a laser, whose electromagnetic radiation is coupled into the channel 144a and leaves the channel 144a at the other end in the shape of a beam cone. The electromagnetic radiation hits the mechanical component 142 which is implemented rotatably around an axis 124. Part of the radiation 146 is reflected by the mechanical component 142, e.g. by a mirroring reflection, and hits the position sensor. The back channels 144b and 144c each receive one part of the electromagnetic radiation 148a and 148b and guide the same to the other end of the position sensor. There, the electromagnetic radiation 148a and 148b guided by the back channels suitably impinges on detectors for electromagnetic radiation 112a and 112b, e.g. photodiodes, coupled to the back channels.

The detectors 112a and 112b convert the radiation 148a and 148b into electrical signals which may be further processed or evaluated by downstream electronics 150. The mechanical component 142 is in its zero position in FIG. 3a, i.e. in a non-deflected state. Based on the symmetrical arrangement of the back channels 144b and 144c with respect to the channel 144a and the rotational axis of the mechanical component, the electromagnetic radiation power 148a and 148b received by the two back channels 144b and 144c is equal or virtually equal. Thus, also the electrical signals generated by the detectors 112a and 112b are equal or virtually equal. If the detectors 112a and 112b are read out differentially or connected to a differential amplifier, then in the non-deflected state an electrical signal equal to zero or virtually zero results.

Figure 3B:
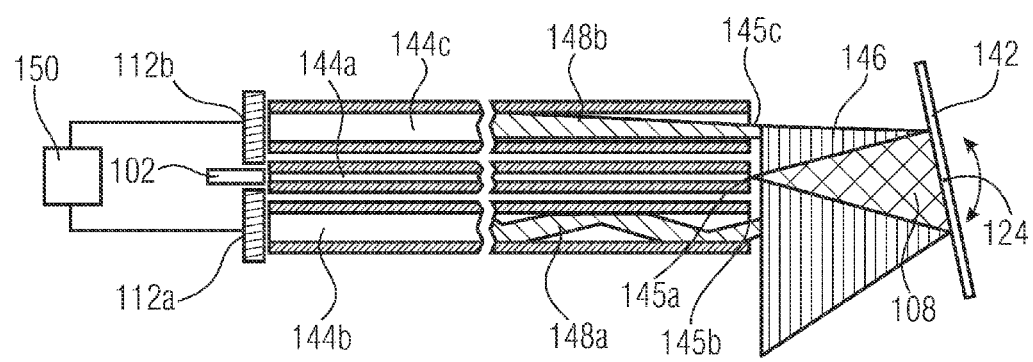

FIG. 3b shows an illustration which represents the functioning of the position sensor of FIG. 1, wherein the mechanical component is deflected from its rest position. The electromagnetic radiation escaping from the output 145a of the channel 144a forms a beam cone 108 with an opening angle determined by the channel 144a, wherein the opening angle is determined by the numerical aperture of the fiber, for example when using an optical fiber. The beam cone 108 impinges on the back side of the movably arranged mechanical component 142, e.g. onto the back side of a microscanner mirror, and is reflected depending on the deflection state. Here, the direction of the reflected beam cone 146 is determined by the reflection law. By the rotation of the mechanical component 142 around the rotational axis 124, the reflected beam cone 146 is reflected in an inclined way onto the position sensor and scans the inputs 145b and 145c of the back channels arranged around the channel 144a depending on the deflection state of the mechanical component 142. The power of the electromagnetic radiation 148a and 148b received by the inputs 145b and 145c of the two back channels 144b and 144c is now different and leads to electrical signals of a different height/intensity in the respective detectors. By amplifying and evaluating the electrical signals of the detectors 112a and 112b of the back channels 144b and 144c, the position or the deflection state of the mechanical component may be determined.

In a differential evaluation of the electrical signals of the detectors, e.g. by a differential amplifier, the result is an electric differential signal whose quantity depends on the deflection angle of the mechanical component. This is caused on the one hand by the non-uniform intensity distribution of the beam cone 108. When using a monomode fiber for the channel 144a, the intensity of the beam cone 108 has a Gaussian distribution, the intensity of the beam cone 108 thus being strongly decreased towards the edge. On the other hand, with larger deflection angles, the edge of the beam cone 108 may scan one of the inputs of the back channels, in FIG. 5b the input 145c of the channel 144c, which additionally leads to a smaller electrical signal. In differential operation, thus an electrical signal results whose sign depends on the deflection direction. Using this principle, it is possible to determine the position or the deflection state of movably arranged mechanical components, like, e.g., of microscanner mirrors, around one or two deflection directions. In this respect, the back channels according to embodiments are arranged symmetrically around the channel which guides the electromagnetic radiation and directs the same at the mechanical component.

For mechanical components which may be pivoted or rotated around a rotational axis, at least two back channels are needed which are arranged regarding their distance perpendicular to the rotational axis of the mechanical component. If the beam cone 108 of the channel 144a, which is implemented to guide electromagnetic radiation and direct the same to the component 142, impinges onto the back side of the mechanical component 142 perpendicularly in the non-deflected state, a rotation or a rotating vibration taking place symmetrically around a rest position of the component 142 also causes a balanced/symmetrical differential signal which comprises a zero crossing in the zero position of the component 142. A non-symmetrical/unbalanced arrangement of the back channels (depending on the mirror size the asymmetry may be some 10 µm to some 100 µm) or a pre-tilting of the back channels with respect to the zero position of the component causes a symmetry shift of the electrical signal. The zero crossing of the electrical signal no longer coincides with the zero position of the component 142. This circumstance is not disadvantageous for the functional principle of the inventive position sensor. By a suitable calibration of the inventive position sensor, such deviations may be compensated. The differential operation of the detectors of opposing back channels, apart from balancing the electrical signal, also offers a suppression of stray or diffused light and DC light. This leads to insensitivity of the position sensor with respect to optical interferences.

Figure 4:
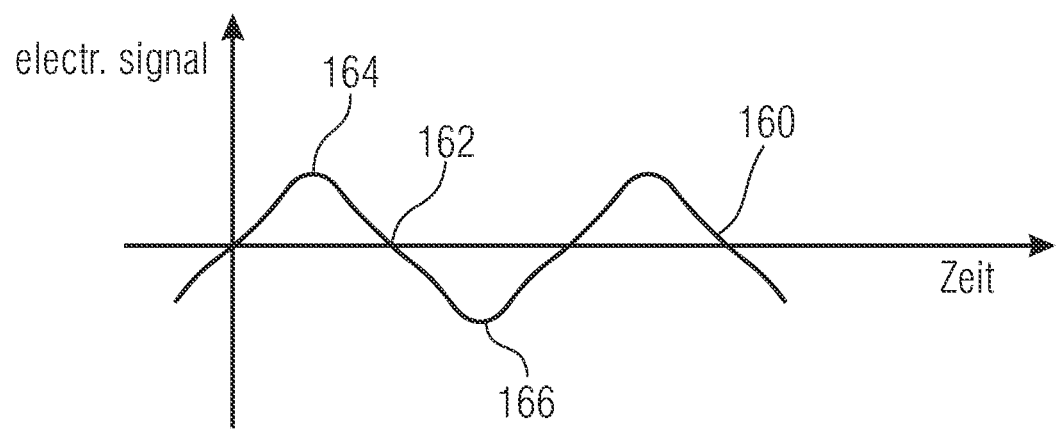
FIG. 4 shows the principal course of a measurement signal of a periodically moved mechanical component, e.g. a microscanner mirror, using a differential amplifier for evaluating the electric signals of the detectors.

FIG. 4 shows the principle course of a measurement signal 160 of a periodically moved mechanical component 142, e.g. of a microscanner mirror, using a differential amplifier for evaluating the electrical signals of the detectors 112a and 112b. The component 142 according to FIGS. 3a and 3b periodically rotates around a rotational axis 124. Due to the symmetry, the zero crossings of the electrical signal 162 correspond to the zero crossing of the component 142. The maxima 164 and minima 166 of the electrical measurement signal 160 each correspond to the turning points of the movement of the component.

Figure 5:
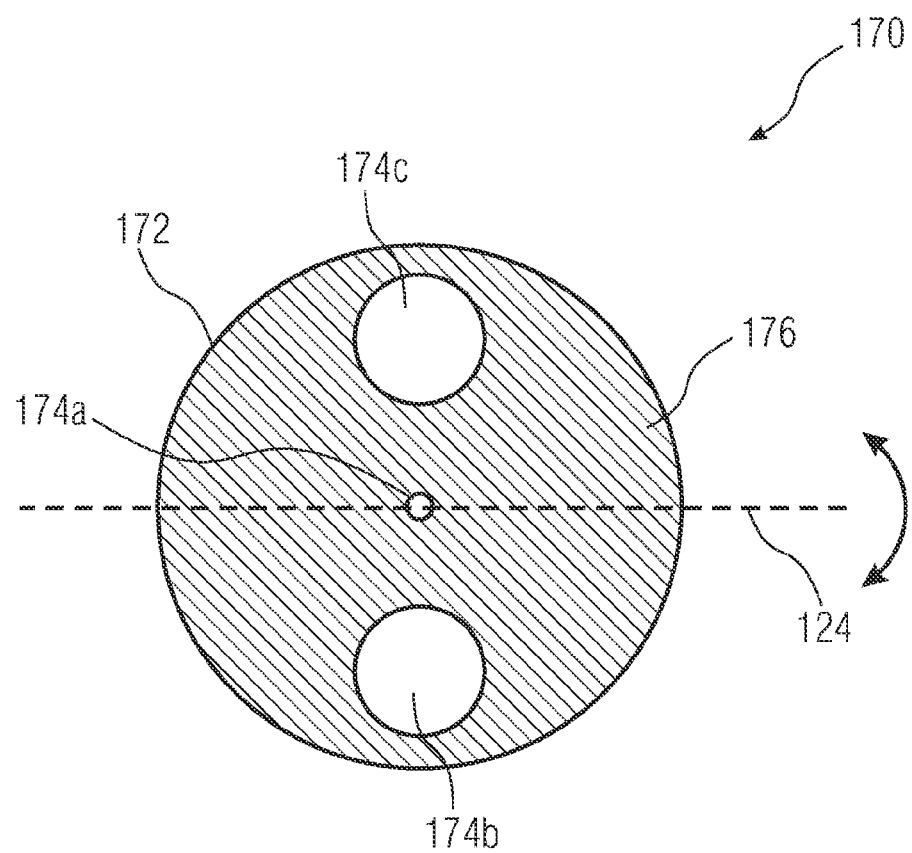
FIG. 5 shows a front view of an optical fiber of the position sensor according to one embodiment, in which the fiber includes three cores.

FIG. 5 shows a front view of an optical fiber of a position sensor according to one embodiment, in which the fiber includes three cores. This is a very advantageous implementation of the fiber bundle 106. Modern methods of fiber manufacturing allow drawing optical fibers using several, possibly also different cores. This variant thus does not represent a classical fiber bundle 106, but rather a fiber 172 of a larger cross-section, in this case with three cores 174a, 174b and 174c and a sheath 176. Similar to FIG. 2, the cores 174b and 174c receiving the electromagnetic radiation reflected by the component are arranged symmetrically around the core 174a and perpendicular to the rotational axis 124 of the mechanical component. The optical fiber 172 having three cores 174a, 174b and 174c illustrated in this embodiment may, e.g., consist of a glass material having step-index profiles.

For mechanical components which are supported rotationally around two rotational axes, at least three, according to embodiments four, back channels are needed.

Figure 6A:
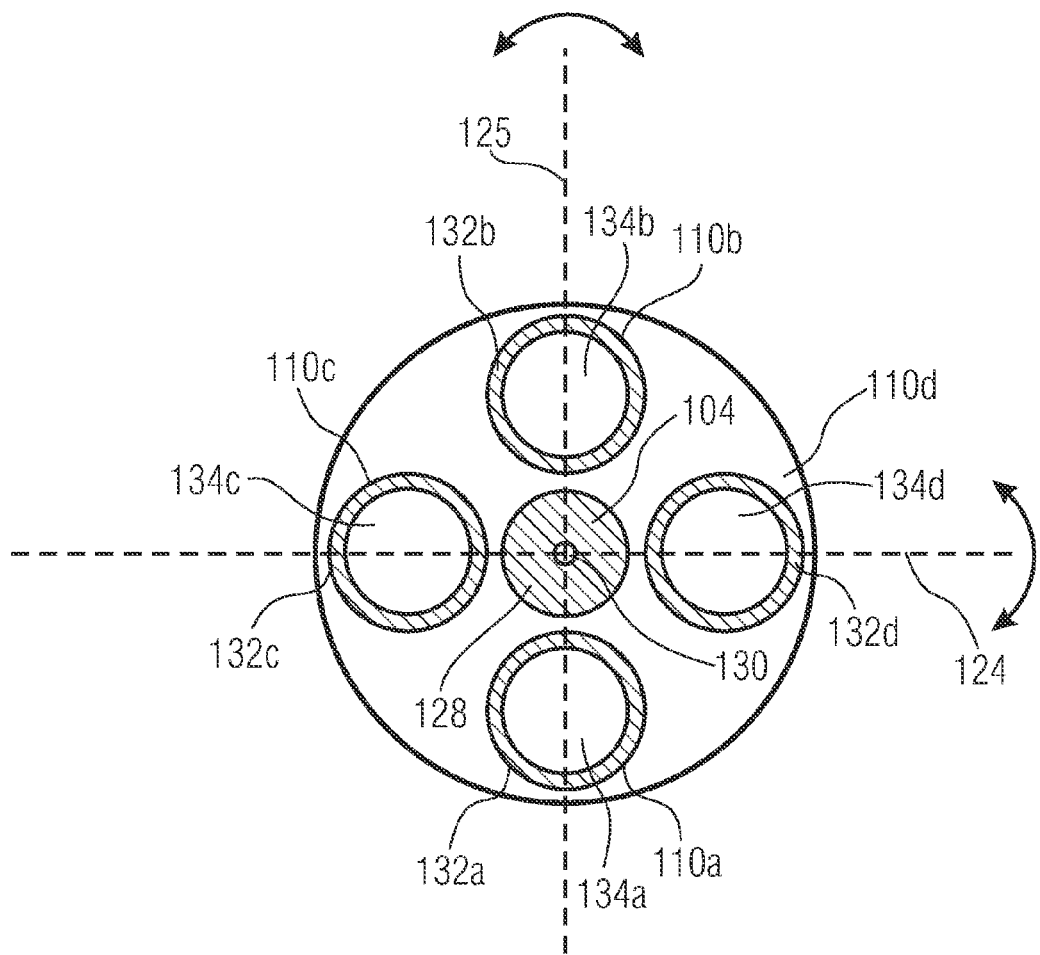
FIG. 6a shows a schematical illustration of the position sensor in a front view according to one embodiment of the invention using a fiber bundle having four receiving fibers for the determination of the deflection state of the mechanical component around two rotational axes.

FIG. 6a shows a schematical illustration of the position sensor in a front view according to one embodiment of the invention using a fiber bundle having four receiving fibers for determining the deflection state of the mechanical component around two rotational axes. The setup is similar to that of FIG. 2. In addition to the transmitting fiber 104 and the receiving fibers 110a and 100b, there are two further receiving fibers 110c and 110d for the determination of the deflection state of the mechanical component around the second rotational axis 125. The receiving fibers 110c and 110d may have the same characteristics as the fibers 110a and 110b. In particular, for the variants illustrated in FIG. 6a, the same implementation possibilities apply as those described in FIG. 2. When using four back channels, according to embodiments, two back channels are each arranged at their distance perpendicular to one rotational axis of the mechanical component each. Further, when using four back channels, the detectors of the respectively opposite back channels may be operated differentially. In this respect, the orientation of the back channels according to embodiments is selected such that the distance lines of opposite back channels coincide with the direction of the rotational axis of the mechanical component.

Figure 6B:
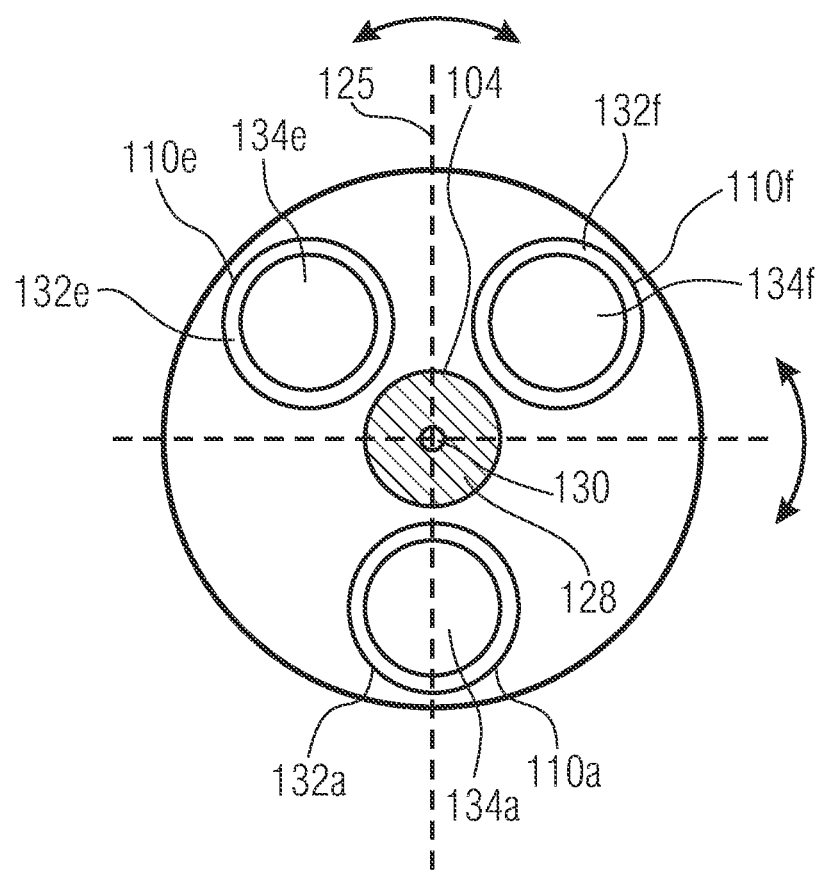
FIG. 6b shows a schematical illustration of the position sensor in a front view according to one embodiment of the invention using a fiber bundle having three receiving fibers for the determination of the deflection state of the mechanical component around two rotational axes.

FIG. 6b shows a schematical illustration of the position sensor in a front view according to one embodiment of the invention using a fiber bundle having three receiving fibers for the determination of the deflection state of the mechanical component around two rotational axes. The setup is very similar to that of FIG. 6a. One transmitting fiber 104 and three receiving fibers 110a, 110e and 110f are used for the determination of the deflection state of a mechanical component around two rotational axes 124 and 125. The receiving fibers 110e and 110f may have the same characteristics as the receiving fibers 110a and 110b of FIG. 6a. In particular, for the variants illustrated in FIG. 6b, the same implementation possibilities apply as those described in FIG. 2.

Figure 7:
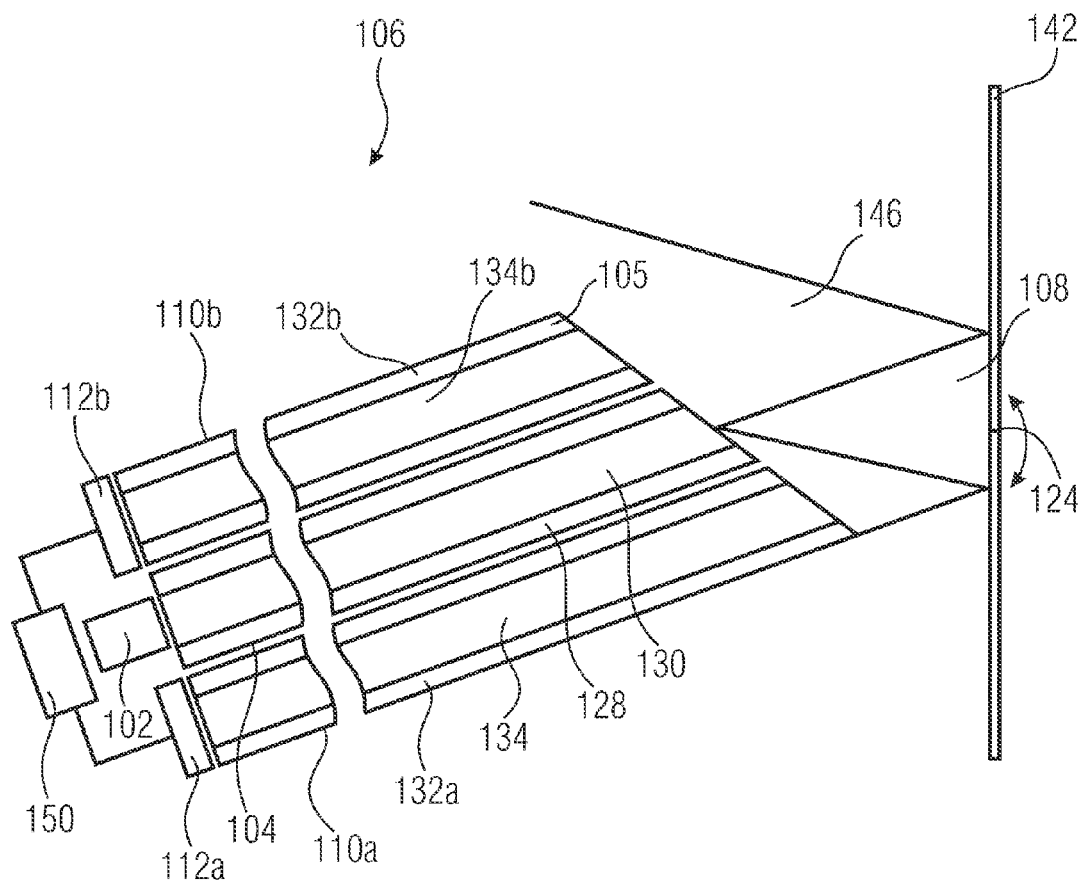
FIG. 7 shows a schematical illustration of the position sensor according to one embodiment of the invention using a fiber bundle having a fiber bundle end of a sloping design for the compensation of the initial deflection state of the mechanical component from its rest position.

FIG. 7 shows a schematical illustration of the position sensor according to an embodiment of the invention using a fiber bundle 106 with a slopingly implemented fiber bundle end 105 for compensating the initial deflection state of the mechanical component from the rest position. The manufacturing of the fiber bundle and in particular the preparation of the fiber bundle end on the side of the component may be executed with common methods of fiber technology. Thus, for generating suitable and defined optical characteristics of the fiber bundle end 105, methods like grinding, polishing and breaking may be used. In particular, the fiber bundle end may also be ground or polished obliquely. This implementation is advantageous when the mechanical component 142 has to be mounted to the fiber axis in a tilted way. In this case, with an inclined or sloping cut of the fiber bundle end 105, the symmetry of the electrical signal may be maintained with respect to the deflection of the mechanical component 142. With a straight cut or break, a tiltedly mounted mechanical component 142 may already lead to a (differential) measurement signal different to zero in the zero position. With an inclined cut, the angle of the radiation output/input into the optical fibers of the fiber bundle 106 is modified such that the tilting of the mechanical component from the zero position is compensated.

Figure 8:
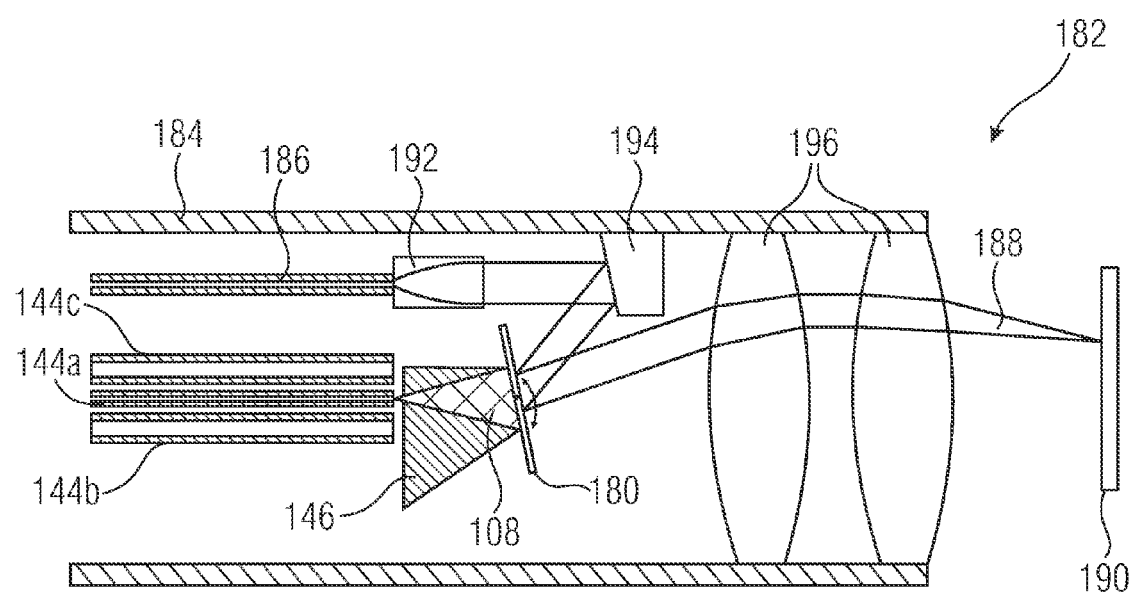
FIG. 8 shows the integration of the inventive position sensor into an endoscope for determining the deflection state of a microscanner mirror.

FIG. 8 shows the integration of the inventive position sensor into an endoscope for determining the deflection state of a microscanner mirror 180. Methods integrated into an endoscope may use a microscanner mirror for scanning the picture field using a laser beam. The resolution and the quality of the gained information are determined by optical circumstances, like, e.g., the numerical aperture and further by the knowledge of the current mirror position. The inventive position sensor may here be very advantageous for determining the deflection state of the microscanner mirror 180 due to its slim design. For this, the back side of the microscanner mirror 180 is used as a reflecting surface. In an outer frame 184 which may, e.g., be made of stainless steel, a microscanner mirror 180 and the inventive position sensor are located, consisting of a channel 144a, for example implemented as an optical transmission fiber, and two back channels 144b, 144c, for example implemented as optical receiving fibers. An electromagnetic radiation 108 exits from the channel 144a, one part of which 146 is reflected by the microscanner mirror 180 and is partially received by the back channels 144b and 144c.

The determination of the deflection state of the microscanner mirror is executed as described above. Further, at the outer frame 184, an optical fiber 186 is located which may be a monomode fiber from which electromagnetic radiation 188 exits, which serves for gaining image information of a measurement object 190. This radiation 188 is collimated by a fiber collimator 192, subsequently hits a deflecting mirror 194 and is guided onto the microscanner mirror 180 by the same. The electromagnetic radiation reflected there is focused onto the measurement object 190 by optical elements 196, for example lenses. Due to the rotational movement of the microscanner mirror 180, the focused beam 188 is guided across the measurement object 190 and thus scans the same. Electromagnetic radiation originating from the measurement object 190, for example by scattering or a fluorescence process, is received by the optical elements 196 and passes through the optical path in the reverse direction. From the knowledge of the current mirror position and the associated intensity of the electromagnetic radiation originating from the object, image information of the measurement object 190 may be reconstructed.

Further embodiments for the inventive position sensor are to be found in many miniaturized systems containing movably or rotatably implemented components of micromechanics (MEMS, MOEMS), manufactured in microtechnology, like, e.g., silicon micromechanics, the LIGA method, plastics technology or a method of precision mechanics. In particular, components containing microscanner mirrors, movable gratings or movable optical or micro-optical components, e.g. polygonal mirrors, etalons or prisms for a specific deflection of electromagnetic radiation. In small laser projectors, with the help of microscanner mirrors, laser light is specifically deflected for image formation. In miniaturized spectrometers and spectrometers for local resolution, small scanner mirrors are used provided with a grid structure as moving refraction gratings. In the field of endoscopy, endomicroscopy and confocal endoscopy, apart from classical methods of image recording or imaging by correspondingly miniaturized optical components in connection with matrix image sensors (CCD and CMOS), a series of scanning methods for gaining additional medically relevant information are gaining ever more importance. Here, in particular laser-based methods are to be mentioned, like confocal microscopy, laser raster microscopy with scanner mirrors and optical coherence tomography.

Embodiments of the invention were described in which the portion of the radiation reflected into the back channels is the same in the rest position of the component. The invention is not restricted to such embodiments, but rather the channel and the back channels may be arranged randomly to each other as long as it is guaranteed that the reflected radiation reaches the back channels so that, e.g., by corresponding calibration measurements, the signal portions guided in the back channels are detected in the rest position of the component and considered in the later measurement.

Further, in the above-mentioned embodiments, the inventive position sensor is used for detecting the deflection state of a rotatably supported mechanical component. The invention is not restricted to these embodiments, however, but rather the inventive position sensor is able to determine the position of a rotatably arranged mechanical component with respect to its original position. Further, the inventive position sensor is not only able to use the electromagnetic radiation reflected by reflection by the mechanical component for the detection of the position of the component, but also the electromagnetic radiation reflected by diffuse reflection or by excitation (e.g. fluorescence). It is further to be noted that the reflected electromagnetic radiation may be changed regarding the polarization direction, for example by a $\lambda/4$ plate.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A deflection state sensor arranged to detect a deflection state of a movably arranged component with respect to its original deflection state, comprising:
   at least one channel which is implemented to guide electromagnetic radiation and direct the same to the component;
   at least one detector; and
   at least two back channels which are implemented to receive electromagnetic radiation reflected by the component and direct the same to the at least one detector; wherein
   the at least one detector comprises a plurality of detector elements;
   each of the at least two back channels is coupled to one of the plurality of detector elements;
   an evaluation circuit is connected to the plurality of detector elements, the evaluation circuit arranged to determine the deflection state of the component with respect to its original deflection state based on signals generated by the plurality of detector elements;
   the at least one channel and the at least two back channels are arranged with respect to each other such that the at least two back channels each receive a predefined portion of the electromagnetic radiation reflected by the component, when the component is in its original deflection state and when the component is in the deflection state to be determined by the evaluation circuit; and
   the component is supported rotatably around at least one axis.

2. The deflection state sensor according to claim 1, wherein the at least one channel comprises an output arranged to output the electromagnetic radiation and wherein each of the at least two back channels comprises an input arranged to receive the electromagnetic radiation, wherein the at least one channel and the at least two back channels are arranged with respect to each other such that the output is located between the inputs and the inputs are arranged symmetrically to the output.

3. The deflection state sensor according to claim 1, wherein the at least one channel is aligned with a rotational axis of the component.

4. The deflection state sensor according to claim 1, comprising at least three back channels for detecting a movement of the component around two rotational axes.

5. The deflection state sensor according to claim 1, comprising a waveguide comprising the at least one channel and the at least two back channels.

6. The deflection state sensor according to claim 5, wherein the waveguide comprises a fiber bundle comprising at least three fibers or one fiber comprising at least three fiber cores.

7. The deflection state sensor according to claim 6, wherein the at least one channel is formed by a monomode fiber or a multimode fiber and wherein the at least two back channels are formed by monomode fibers or multimode fibers.

8. The deflection state sensor according to claim 5, wherein an end of the waveguide adjacent to the component is oblique.

9. The deflection state sensor according to claim 5, wherein the waveguide generates the electromagnetic radiation.

10. The deflection state sensor according to claim 1, comprising an electromagnetic radiation source which is coupled to the at least one channel.

11. The deflection state sensor according to claim 1, wherein the evaluation circuit is implemented to differentially evaluate the signals received from the plurality of detector elements.

12. The deflection state sensor according to claim 1, wherein the component comprises a mechanical component, a micromechanical component, a microscanner mirror, a refraction grating, an optical component, a micro-optical component, an etalon, or a prism.

13. A device comprising:
   a movably arranged component which is supported rotatably around at least one axis; and
   a deflection state sensor arranged to detect a deflection state of the component with respect to its original deflection state, wherein the deflection state sensor includes:
      at least one channel which is implemented to guide electromagnetic radiation and direct the same to the component;
      at least one detector; and
      at least two back channels which are implemented to receive electromagnetic radiation reflected by the component and direct the same to the at least one detector; wherein
   the at least one detector comprises a plurality of detector elements;
   each of the at least two back channels is coupled to one of the plurality of detector elements;
   an evaluation circuit is connected to the plurality of detector elements, the evaluation circuit arranged to determine a deflection state of the component with respect to its original deflection state based on signals generated by the plurality of detector elements; and
   the at least one channel and the at least two back channels are arranged with respect to each other such that the at least two back channels each receive a predefined portion of the electromagnetic radiation reflected by the component, when the component is in its original deflection state and when the component is in the deflection state to be determined by the evaluation circuit.

14. The device according to claim 13, wherein the device is an image recording system, a projection system, an endoscope, an endomicroscope, a confocal endoscope, a laser microscope, a confocal laser microscope, a spectrometer, a spectrometer with local resolution, or a coherence tomography unit.

* * * * *